United States Patent
Llacer

(10) Patent No.: US 7,027,557 B2
(45) Date of Patent: Apr. 11, 2006

(54) METHOD FOR ASSISTED BEAM SELECTION IN RADIATION THERAPY PLANNING

(76) Inventor: Jorge Llacer, 130 Forest Hill Dr., Los Gatos, CA (US) 95032

( * ) Notice: Subject to any disclaimer, the term of this patent is extended or adjusted under 35 U.S.C. 154(b) by 141 days.

(21) Appl. No.: 10/845,614

(22) Filed: May 13, 2004

(65) Prior Publication Data

US 2005/0254622 A1     Nov. 17, 2005

(51) Int. Cl.
*A61N 5/10* (2006.01)
(52) U.S. Cl. ...................................................... 378/65
(58) Field of Classification Search ............... 378/65
See application file for complete search history.

(56) References Cited

U.S. PATENT DOCUMENTS

| | | | | |
|---|---|---|---|---|
| 3,987,281 | A * | 10/1976 | Hodes | 600/407 |
| 5,651,043 | A * | 7/1997 | Tsuyuki et al. | 378/65 |
| 5,754,623 | A * | 5/1998 | Seki | 378/65 |
| 5,778,043 | A * | 7/1998 | Cosman | 378/65 |
| 5,818,902 | A | 10/1998 | Yu | |
| 6,260,005 | B1 | 7/2001 | Yang | |
| 6,504,899 | B1 | 1/2003 | Pugachev | |
| 6,661,872 | B1 | 12/2003 | Bova | |
| 2004/0165696 | A1* | 8/2004 | Lee | 378/65 |
| 2005/0111621 | A1* | 5/2005 | Riker et al. | 378/65 |
| 2005/0207531 | A1* | 9/2005 | Dempsey et al. | 378/65 |

OTHER PUBLICATIONS

J. Llacer, "Comparative Behaviour of the Dynamically Penalized Likelihood algorithm in inverse radiation therapy planning", Phys. Med. Biol., vol. 46, (2001) 2637-2663.

S. Soderstrom, A. Brahme, "Selection of suitable beam orientations in radiation therapy using entropy and Fourier transform measures", Phys. Med. Biol., vol. 37, (1992) 911-924.

T. Bortfeld and W. Schlegel, "Optimization of beam orientations in radiation therapy: some theoretical considerations", Phys. Med. Biol., vol. 38, (1993), 291-304.

P. Gokhale, et al, "Determination of beam orientation in radiotherapy planning", Med. Phys., vol. 21 (3), (1994), 393-400.

(Continued)

*Primary Examiner*—Edward J. Glick
*Assistant Examiner*—Anastasia Midkiff

(57) ABSTRACT

A method to assist in the selection of optimum beam orientations for radiation therapy when a planning treatment volume (PTV) is adjacent to one or more organs-at-risk (OARs). A mathematical analysis of the boundaries between the PTV and OARs allows the definition of a continuum of pairs of gantry and table angles whose beam orientations have planes that are essentially parallel to those boundaries, and can, therefore, separate the PTV from the OARs when a multi-leaf collimator is used in the therapy. The Radiation Oncologist can then select one or more pairs of gantry and table angles from the continuum as input to a beam optimization step. The selected angles can deliver highly uniform dose to the PTV, while minimizing the radiation dose to the OARs.

14 Claims, 13 Drawing Sheets

OTHER PUBLICATIONS

S. Webb, "Optimizing the planning of intensity-modulated radiotherapy", Phys. Med. Biol., vol. 39, (1994), 2229-2246.

S.M. Morrill, et al, "Conventional treatment planning optimization using simulated annealing", Int. J. Rad. Oncol. Biol. Phys., vol. 32, Supplement 1, (1994), 298.

Soderstrom and A. Brahme, Which is the most suitable number of photon beam portals in coplanar . . . ?, Int. J. Rad. Oncol. Biol. Phys., vol. 33, No. 1, (1995) 151-159.

D.L. McShan, et al, Advanced interactive planning techniques for conformal therapy: high level beam . . . , Int. J. Rad. Oncol. Biol. Phys., vol. 33, No. 5(1995) 1061-1072.

C.X. Yu, "Intensity-modulated arc therapy with dynamic multileaf collimation: an alternative to tomotherapy", Phys. Med. Biol., vol. 40 (1995) 1435-1449.

T.R. Mackie, et al, "Tomotherapy: A new concept for the delivery of dynamic conformal radiotherapy", Med, Phys., vol. 20 (6), (1993), 1709-1719.

G.A. Ezzell, "Genetic and geometric optimization of three-dimensional radiation therapy treatment planning", Med. Phys., vol. 23 (3) (1996) 293-305.

M. Langer, et al, in "A generic genetic algorithm for generating beam weights", Med. Phys., vol. 23 (6), (1996), 965-971.

V. C. Ling, et al, in "Conformal radiation treatment of prostate cancer using inversely-planned . . . ", Int. J. Rad. Oncol. Biol. Phys., vol. 35, No. 4, (1996) 721-730.

S.K. Das and L.B. Marks, in "Selection of coplanar or noncoplanar beams using three-dimensional . . . ", Int. J. Rad. Oncol. Biol. Phys., vol. 38, No. 3, (1997), 643-655.

Lu, et al, in "Optimized beam planning for linear accelerator-based stereotactic radiosurgery", Int. J. Rad. Oncol. Biol. Phys., vol. 39, No. 5, (1997), 1183-1189.

O.C.L. Haas, et al, "Optimization of beam orientation in radiotherapy using planar geometry", Phys.Med. and Biol., vol. 43 (1998), 2179-2193.

B.C.J. Cho, et al, The development of target-eye-view maps for selection of coplanar or noncoplanar beams . . . , Med. Phys., vol. 26, (11) (1999) 2367-2374.

C.G. Rowbottom, et al, "Constrained customization of non-coplanar beam orientations in radiotherapy of brain tumors", Phys. Med. Biol., vol. 44 (1999) 383-399.

M.E. Hosseini-Ashrafe, et al, "Pre-optimization of radiotherapy treatment planning: an artificial neural network . . . ", Phys. Med. Biol., vol. 44 (1999) 1513-1528.

C.G. Rowbottom, et al, "Beam orientation customization using an artificial neural network", Phys. Med. Biol., vol. 44 (1999), 2251-2262.

M. Braunstein and R.Y. Levine, "Optimum beam configurations in tomographic intensity modulated radiation therapy", Phys. Med. and Biol., No. 45 (2000), 305-328.

O. Jakel and J. Debus, "Selection of beam angles for radiotherapy of skull base tumours using charged particles", in Phys. Med. Biol., vol. 45 (2000) 1229-1241.

A.B. Pugachev, et al, "Beam orientation optiimization in intensity-modulated radiation treatment planning", Med. Phys., vol. 27 (6) (2000), 1238-1245.

A. V. Pugachev, et al, "Role of beam orientation optimization in intensity-modulated radiation therapy", Int. J. Rad. Oncol. Biol. Phys. vol. 50, No. 2 (2001), pp. 551-560.

A. Pugachev and L. Xing, "Pseudo beam's-eye-view as applied to beam orientation selection . . . ", Int. J. Rad. Oncol. Biol. Phys. vol. 51, No. 5, (2001) 1361-1370.

A. Pugachev and L. Xing. "Computer-assisted selection of coplanar beam orientations in intensity-modulated . . . ", Phys. in Med. and Biol., vol. 46, (2001) 2467-2476.

A. Pugachev and L. Xing, "Incorporating prior knowledge into beam orientation optimization in IMRT",, Int. J. Rad. Oncol. Biol. Phys. vol. 54, No. 5 (2002), 1565-1574.

E. Woudstra and PRM Storchi, "Constrained treatment planning using sequential beam selection", Phys. in Med. and Biol., vol. 45 (2000), 2133-2149.

C.G. Rowbottom, et al, "Simultaneous optimization of beam orientations and beam weights in conformal therapy" Med. Phys. vol. 28 (8) (2001), 1696-1702.

X. Wu and Y. Zhu "A mixed-encoding genetic algorithm with beam constraint for conformal radiotherapy treatment planning", Med, Phys., vol. 27 (11) (2000), 2508-2516.

P. Zhang, et al, "Optimization of Gamma Knife treatment planning via guided evolutionary simulated annealing", Med. Phys., vol. 28 (8) (2001) 1746-1752.

Y. Li, et al, "Automatic beam angle selection in IMRT planning using genetic algorithm", Phys. Med. Biol., vol. 49 (2004), 1915-1932.

D. Djajaputra, et al, "Algorithm and performance of a clinical IMRT beam-angle optimization system", Phys. Med. Biol., vol. 48 (2003),3191-3212.

* cited by examiner

|Grad| PTV

|Grad| OAR

Overlap

Overlap mask

Axial views

Plane 1

Plane 3

Plane 6

Plane 7

Plane 10

Plane 13

Plane 50

METHOD FOR ASSISTED BEAM SELECTION IN RADIATION THERAPY PLANNING

BACKGROUND OF THE INVENTION

1. Field of the Invention

The invention relates to radiation therapy planning for the treatment of tumors or for stereotactic radiosurgery and more particularly to assist in the selection of optimum beam orientations for that therapy.

2. Description of Prior Art

The goal of radiation therapy is the accurate delivery of a radiation dose to tumors or other abnormal tissues in the human body to cause their obliteration, while keeping the dose received by sensitive organs and/or normal tissues to a tolerable minimum. Four main methods of radiation delivery are in use at the present time: Conformal, Intensity Modulated, Dynamic Arc and Tomotherapy. The Conformal method uses a relatively small number of radiation beams, each having a perimeter that conforms to the external shape of the abnormal tissues, as seen from the direction of the incoming beam. In Intensity Modulated Radiation Treatment (IMRT), each of the conformal beams is broken into a large number of pencil beams, or "beamlets", and the dose delivered by each beamlet is controlled independently. In Dynamic Arc therapy, radiation is delivered by a source that travels continuously along one or more arcs partially surrounding the patient, with the shape of the radiation field changing continuously as needed to remain conformal to the perimeter of the abnormal region. In Tomotherapy, a "fan beam" of radiation rotates about the patient with the width of the fan controlled to conform to the shape of the abnormal tissues as it progresses, not only around the patient, but traveling along his/her length. In all cases, the sum of the doses delivered to each voxel of the abnormal tissues by all beams or beamlets is expected to be close to a prescribed dose, while the total dose delivered to voxels in sensitive organs and/or normal tissues has to be kept within some acceptable prescribed limits.

In the four methods indicated above, the abnormal tissues are included in a Planning Target Volume (PTV), located usually at the center of rotation of a radiation delivery system. With that approach, radiation coming from all the chosen orientations will always add up to a maximum dose in the PTV, while the dose to Organs-at-Risk (OARs) and/or normal tissues in the periphery can be lower.

Except in the case of Tomotherapy, where radiation always impinges on the PTV from all the angles around a circle, the selection of beam angles is of principal importance in radiation therapy. The experience of the Radiation Oncologist has traditionally been a most important factor in the successful planning of therapy for any particular clinical case. As will be described below, however, substantial efforts have been made to automate the selection of beam orientation angles to avoid a time-consuming "trial-and-error" process that is often required when a new location and/or shape of abnormality has to be treated. It is in this step of beam orientation angle selection that the present invention is expected to be of substantial assistance to the Radiation Oncologist.

Once a set of beam orientation angles has been selected, the next step is an "optimization" phase: The individual fluences to be delivered by each of the defined beams, beamlets or arcs, the so-called "beam weights", have to be determined. In the case of IMRT and Tomotherapy, the determination of the optimum beamlet weights may require the solution of a set of a few thousand inconsistent simultaneous equations, usually with inequalities. Methods for the successful solution of the optimization problem have been found and are in use in a number of commercial software packages and in research institutions. For the case of IMRT, a comparison of one example each of the three most commonly used optimization methodologies is given in J. Llacer, et al, "*Comparative Behaviour of the Dynamically Penalized Likelihood algorithm in inverse radiation therapy planning*", Physics in Medicine and Biology, Vol. 46, (2001), pp. 2637–2663.

We must now return to the previous step of determining the optimal beam orientations. As indicated above, a substantial scientific effort has been placed on finding suitable methods for such determination, prior to beam weight optimization. A brief description of those efforts will now be outlined. With some exceptions to be noted, all the methods have resorted to simplified optimizations and their comparison by a variety of measures, with or without some evolutionary means to improve the results as the selection proceeds towards a final solution. In general, the methods shown yield better optimizations than some reference set of beams, although they are very expensive in computer time and have not found sufficient favor in clinical applications.

S. Söderstrom and A. Brahme in "*Selection of suitable beam orientations in radiation therapy using entropy and Fourier transform measures*", Physics in Medicine and Biology, Vol. 37, (1992), pp. 911–924, use entropy and also the integral of the low frequency part of the Fourier transform of optimum "beam profiles" (a profile of contiguous beam weights) as measures of the information content in those profiles and the amount of gross beam structure, respectively. T. Bortfeld and W. Schlegel in "*Optimization of beam orientations in radiation therapy: some theoretical considerations*", Physics in Medicine and Biology, Vol. 38, (1993), pp. 291–304, use simulated annealing in frequency domain and arrive at the conclusion that, for multiple-beam irradiation (more than three beams) the optimum beam configuration tends to be an even distribution over an angular range of 0 to 2π. P. Gokhale, et al, in "*Determination of beam orientation in radiotherapy planning*", Medical Physics, Vol. 21 (3), (1994), pp. 393–400 use mathematical techniques to determine the "path of least resistance" from the PTV to the patient surface and select the beams with lowest resistance. S. Webb in "*Optimizing the planning of intensity-modulated radiotherapy*", Physics in Medicine and Biology, Vol. 39, (1994), pp. 2229–2246, arrives at the conclusion that the use of 7 to 9 uniformly spaced beam directions can lead to acceptable optimizations, except when the PTV and OARs overlap. He provides a comment, but no solution for, the problem of optimizing field orientation. S. M. Morrill, et al, in "*Conventional treatment planning optimization using simulated annealing*", Int. J. Radiation Oncology Biol. Phys., Vol 32, Supplement 1, (1994), p. 298, describes the reduction of needed beam angles to a relatively small number by simulated annealing as the optimization phase proceeds. S. Söderstrom and A. Brahme in "*Which is the most suitable number of photon beam portals in coplanar radiation therapy?*, Int. J. Radiation Oncology Biol. Phys., Vol 33, No. 1, (1995), pp. 151–159 reach the conclusion that with non-uniform beams (IMRT), the level of complication-free tumor control is adequate with 3 beams to 5 beams and more beams do not result in substantial improvements. D. L. McShan, et al, in "*Advanced interactive planning techniques for conformal therapy: high level beam descriptions and volumetric mapping techniques*", Int. J. Radiation Oncology Biol. Phys., Vol 33, No. 5, (1995), pp.

1061–1072, describes the use of "Beam's Eye Volumetrics", a graphical interactive method to define a PTV and OARs in terms of arcs, cones and other shapes. Those shapes can then be used to aid in the selection of beams for conformal therapy.

C. X. Yu in "*Intensity-modulated arc therapy with dynamic multileaf collimation: an alternative to tomotherapy*", Physics in Medicine and Biology, Vol. 40 (1995) pp. 1435–1449 and U.S. Pat. No. 5,818,902 "*Intensity modulated arc therapy with dynamic multi-leaf collimation*", (Oct. 6, 1998) describe a "hybrid" between Tomotherapy and Dynamic Arc therapy in which a gantry stops at a number of selected angles around the patient. Tomotherapy is described in T. R. Mackie, et al, "*Tomotherapy: A new concept for the delivery of dynamic conformal radiotherapy*", Medical Physics, Vol 20 (6), (1993), pp. 1709–1719.

G. A. Ezzell in "*Genetic and geometric optimization of three-dimensional radiation therapy treatment planning*", Medical Physics, Vol. 23 (3) (1996) pp. 293–305, describes what appears to be the first application of genetic algorithms to optimization. Together with geometric considerations for the elimination of "undesirable" beamlets, it reaches optimization angles and weights that lead to reasonable optimizations. M. Langer, et al, in "*A generic genetic algorithm for generating beam weights*", Medical Physics, Vol. 23 (6), (1996), pp. 965–971, describe the use of a genetic algorithm for the optimization of up to 36 beams (or beamlets) for the treatment of abdominal tumors.

V. C. Ling, et al, in "*Conformal radiation treatment of prostate cancer using inversely-planned intensity-modulated photon beams produced with dynamic multileaf collimation*", Int. J. Radiation Oncology Biol. Phys., Vol. 35, No. 4, (1996), pp. 721–730 report promising results by the use of six co-planar beams for the treatment of prostate cancer. Those beams are pair-wise opposed at −45°, 0° and +45° with respect to the horizontally placed patient. S. K. Das and L. B. Marks, in "*Selection of coplanar or noncoplanar beams using three-dimensional optimization based on maximum beam separation and minimized nontarget irradiation*", Int. J. Radiation Oncology Biol. Phys., Vol. 38, No. 3, (1997), pp. 643–655 report on the use of two measures for the selection of beam angles: maximum beam separation for steep dose gradient at target edge and a length function related to normal tissue traversed by a beam. By a suitable combination of those measures, reasonable sets of beam angles are found for clinical situations. H-M. Lu, et al, in "Optimized beam planning for linear accelerator-based stereotactic radiosurgery", Int. J. Radiation Oncology Biol. Phys., Vol. 39, No. 5, (1997), pp. 1183–1189, use a Beam's Eye View of possible beam arc combinations and phase-space scrutiny to reduce the available angles. Finally, a simulated annealing method yields the optimal beam angles.

O. C. L. Haas, et al, in "*Optimization of beam orientation in radiotherapy using planar geometry*", Physics in Medicine and Biology, Vol. 43 (1998), pp. 2179–2193, returns to the use of a genetic algorithm specifically for coplanar beams, using a methodology that allows the algorithm to search in parallel for different objectives, resulting in a speed up of the search. B. C. J. Cho, et al, in "*The development of target-eye-view maps for selection of coplanar or noncoplanar beams in conformal radiotherapy treatment planning*", Medical Physics, Vol. 26, (11), (1999) pp. 2367–2372, use Beam's Eye View (BEV) techniques together with a Target's Eye View (TEV) to map the OARs and check for regions of overlap with the PTV in a Mercator spherical map, thus assisting visually in a computer screen to select beam orientations that present minimum conflicts. C. G. Rowbottom, et al, in "*Constrained customization of non-coplanar beam orientations in radiotherapy of brain tumors*", Physics in Medicine and Biology, Vol. 44 (1999) pp. 383–399, used a methodology consisting of single and multibeam cost functions, together with simulated annealing to produce well-spaced, customized beam orientations for individual patients.

M. E. Hosseini-Ashrafe, et al, in "*Pre-optimization of radiotherapy treatment planning: an artificial neural network classification aided technique*", Physics in Medicine and Biology, Vol. 44 (1999) pp. 1513–1528, introduce artificial neural networks to the problem of beam selection, an approach that is also followed by C. G. Rowbottom, et al, in "*Beam orientation customization using an artificial neural network*", Physics in Medicine and Biology, Vol. 44 (1999) pp. 2251–2262. The initial use of neural networks for the beam selection problem has not been followed in later years.

M. Braunstein and R. Y. Levine, in "*Optimum beam configurations in tomographic intensity modulated radiation therapy*", Physics in Medicine and Biology, No. 45 (2000), pp. 305–328, have tested a method of ranking particular beam orientations in terms of the contributed dose to the PTV and OARs. For simple simulated clinical cases, they find that there are, indeed, preferred beam directions. O. Jäkel and J. Debus, in "*Selection of beam angles for radiotherapy of skull base tumours using charged particles*", in Physics in Medicine and Biology, Vol. 45 (2000) pp. 1229–1241, analyze the beams selected in 50 patients treated by conformal therapy with X-rays and arrive at a consensus of which beam orientations should then be used for treatments with charged particles.

The next group includes a number of papers and a Patent by A. B. Pugachev and co-workers at Stanford University. Their work follows a progression towards a final method that could be applied in the clinic. It is characterized initially by simplified optimizations and later by progressively simpler and better search methods based on the geometry of the PTV and OARs. A. B. Pugachev, et al, "*Beam orientation optimization in intensity-modulated radiation treatment planning*", Medical Physics, Vol. 27 (6) (2000), pp. 1238–1245; A. V. Pugachev, et al, "*Role of beam orientation optimization in intensity-modulated radiation therapy*", Int. J. Radiation Oncology Biol. Phys. Vol. 50, No. 2 (2001), pp. 551–560; A. Pugachev and L. Xing, "*Pseudo beam's-eye-view as applied to beam orientation selection in intensity-modulated radiation therapy*", Int. J. Radiation Oncology Biol. Phys. Vol. 51, No. 5 (2001), pp. 1361–1370; A. Pugachev and L. Xing, "*Computer-assisted selection of coplanar beam orientations in intensity-modulated radiation therapy*", Physics in Medicine and Biology, Vol. 46, (2001), pp. 2467–2476 and U.S. Pat. No. 6,504,899, "*Method for selecting beam orientations in intensity modulated radiation therapy*", (Jan. 7, 2003); A. Pugachev and L. Xing, "*Incorporating prior knowledge into beam orientation optimization in IMRT*", ", Int. J. Radiation Oncology Biol. Phys. Vol. 54, No. 5 (2002), pp. 1565–1574.

E. Woudstra and P R M Storchi, in "*Constrained treatment planning using sequential beam selection*", Physics in Medicine and Biology, Vol. 45 (2000), pp. 2133–2149, have developed a method based on pre-calculated dose distributions for all candidate orientations and a sequential method to add beams into the selection by a scoring method. C. G. Rowbottom, et al, in "*Simultaneous optimization of beam orientations and beam weights in conformal therapy*" Medical Physics Vol. 28 (8) (2001) pp. 1696–1702, have developed an optimization algorithm for both beam orientations and beam weights based on a random sampling of the PTV and OAR voxels which produce acceptable dose distributions and may be able to improve on those obtained by human planners. In T. Y. Yang, et al, U.S. Pat. No. 6,260,005, "*Falcon: Automated optimization method for arbitrary assessment criteria*", (Jul. 10, 2001) a complete optimization methodology is described that is applied to radiation therapy as an example. The orientation of the therapy beams is not generated by the method, but has to be given by the user.

Genetic algorithms for beam orientation optimization have reappeared: X. Wu and Y. Zhu in "*A mixed-encoding genetic algorithm with beam constraint for conformal radiotherapy treatment planning*", Medical Physics, Vol. 27 (11) (2000) pp. 2508–2516 propose a new hierarchical algorithm that combines binary and floating-point encoding to both select beam directions and beam weights. P. Zhang, et al, in "*Optimization of Gamma Knife treatment planning via guided evolutionary simulated annealing*", Medical Physics, Vol. 28 (8) (2001) pp. 1746–1752 use a guided evolutionary simulated annealing method that yields results in a more conformal plan and reduces treatment administration time, in comparison with manual methods. Y. Li, et al, in "*Automatic beam angle selection in IMRT planning using genetic algorithm*", Physics in Medicine and Biology, Vol. 49 (2004), pp. 1915–1932, separate the genetic selection part of the problem from the optimization and can carry out both in reasonable times, yielding sensible results that may be clinically useful.

D. Djajaputra, et al, in "*Algorithm and performance of a clinical IMRT beam-angle optimization system*", Physics in Medicine and Biology, Vol. 48 (2003) pp. 3191–3212 have accelerated the processes of dose calculation, optimization and beam selection by simplification and the use of pre-computed dose kernels. They still report many hours of computation for relatively complex therapy cases. Finally, F. J. Bova in U.S. Pat. No. 6,661,872, "*Intensity modulated radiation therapy planning system*", (Dec. 9, 2003) describes a method for beam selection that relies on replacing arcs, as in Dynamic Arc therapy, with a number of equally spaced source positions along the arcs and then using a scoring system to define which positions are to be kept in a final beam selection.

It is recognized by workers in the area of beam orientation optimization that the problem is a very difficult one to solve in a satisfactory manner within a computation time that is useful in the clinic. Of all the work reviewed above, only the object of U.S. Pat. No. 6,504,899, issued Jan. 7, 2003 to Pugachev and Xing, appears to have a chance of being used extensively in the foreseeable future for beam selection in the clinic. Their method does indeed select beam orientations that are reasonable, within the time constraints imposed by clinical practice. The method of Pugachev and Xing, however, suffers from the severe limitation that is only applicable to therapy with coplanar beams, that is, beams that originate in a radiation source that can move along the perimeter of a circle. In the frequent cases of therapy for tumors or other abnormalities in the head and/or into the neck area, therapy beams can be delivered from non-coplanar beams, that is from a source that can move on the surface of a sphere, except for positional conflicts with the neck. The ability to select such non-coplanar beams is a necessity in order to achieve treatment plans that yield the desired high dose to the PTV and provide adequate sparing of the very sensitive organs and healthy tissues in the head, for example.

The extension of Pugachev and Xing's method to non-coplanar beams is prohibitive, as would be the case with all the other selection methods reviewed above. The extremely high increase in the number of possible candidate beam orientations in going from a circular set of source positions to a spherical one results in an inordinate increase in computation time.

The main cause of difficulty with all the attempts at solving the beam selection problem is the overly ambitious goal that has been set, that of selecting automatically all the beams that should be used in the optimization of a particular clinical case. What has been overlooked is that an appropriate computational analysis of the geometry of the PTV and OARs provides a wealth of information that can be used to select several very important coplanar or non-coplanar beam orientations in a number of difficult clinical cases, particularly those in which one or more OARs are adjacent to the PTV. The use of beam's or target's eye views and projections of the PTV and OARs onto spherical or cylindrical surfaces, as in some of the work reviewed above, are steps in the desired direction and such methods have been incorporated extensively in commercial treatment planning software packages. Those methods, however, do not use make good use of the capabilities of current computational techniques in Computer Vision, which can provide more accurate and complete information about the nature of the boundaries between a PTV and any adjacent OARs. Such information will be shown to allow the selection of beam orientations yielding optimizations that may be limited only by fundamental radiation physics.

SUMMARY OF THE INVENTION

The present invention is a method for the selection of a number of beam orientations in radiation therapy that fulfill the requirement of fully irradiating the Planning Target Volume (PTV) of a patient while sparing one or more adjacent Organs-at-Risk (OARs) to the maximum extent allowed by the physics of the particular type of radiation used. The invention uses techniques derived from Computer Vision to allow the computer to examine the boundaries between volumetric representations of the PTV and OARs and present the Radiation Oncologist with a continuum of choices along one or more preferred arcs of beam orientations. The Radiation Oncologist can then examine those arcs and, for Conformal and IMRT therapy, select a number of beam orientations from them that present no conflicts with any of the many factors that his/her experience indicate could result in a less than desirable treatment. Additional beam orientations can also be added as the Radiation Oncologist sees fit. For Dynamic Arc therapy, those preferred arcs can be used directly.

Specifically the preferred implementation of the invention includes a method and apparatus for selecting optimum beam orientations by using a set of mathematical operators generally known as "Gaussian Invariants" that allow a computer to examine three-dimensional objects and extract a number of features from their representation, as edges, corners, ridges, tangents and many more. Those operators are based on convolutions of the object representation with partial derivatives of Gaussians of different size, or standard deviation. The term "Invariant" refers to the requirement that the extracted features have to remain invariant under rotation and translation of the object, at least. The simplest operator can be termed the L operator, which takes the representation of an object as a three-dimensional matrix of intensities, densities, or whatever variable the object represents and convolves it with a three-dimensional Gaussian. The standard deviation of the Gaussian is termed the "scale" of a representation. At small scale, L returns a somewhat blurred view of the object and at large scales, most of the fine structures of the object have disappeared and one can only see a "blob" giving the general shape of the object.

Using the standard Euclidean three-dimensional representation, operating with $L_x$ corresponds to the convolution of the object with the partial derivative in the x-direction of a Gaussian at the scale chosen. Similarly for other directions and more complex operators. $L_{xyy}$, for example, is an operator that convolves an object with the partial derivative in the x-direction and the second partial derivative in the y-direction of a three-dimensional Gaussian.

The preferred method and apparatus comprises a computer running a program whose first step is the representation of the PTV and OAR by two separate three-dimensional regions of uniform, non-zero density embedded in respective three-dimensional matrices of otherwise zero density. The PTV and OAR matrices are next convolved with the gradient magnitude operator Grad, defined as $$\text{Grad} = \sqrt{L_x^2 + L_y^2 + L_z^2}$$

that extracts a blurred form of the edges of the respective regions. The amount of blurring is controlled by the scale of the operation. Because of that blurring, there is an overlap in the resulting Grad matrices in the region in which the PTV is adjacent to the OAR. That overlap region acts as a "mask" for the operations to follow.

The next step in the preferred embodiment consists in finding the tangents to the PTV in the region of overlap inside the OAR in a computer readable form. The gauge coordinate w of Gaussian Invariant theory, applied to the Grad of the PTV and OAR, returns a vector in Euclidean space that is tangential to the ridge formed by the Grad operator in the region of overlap. The computation returns two matrices containing the x- and y-components of the tangent vectors, respectively. That computation is carried out by operating with $L_y$ on the masked Grad image for the x-component of the tangent vector and with $-L_x$ for the y-component, that is, $$w = \begin{bmatrix} L_y \\ -L_x \end{bmatrix}$$

with L now being the matrix of the Grad for the PTV or the OAR. A vector $\alpha$ at each one of the non-zero voxels of w represents the direction of the tangent to a plane in the interface between the PTV and the OAR as seen by an observer facing the [x-y] plane of the PTV and OAR regions.

The matrices representing the PTV and OAR are then rotated so that an observer would be facing the [x-z] plane, for example, and the above operations are repeated yielding a second vector $\beta$ at each voxel of w representing the direction of the tangent to the interface plane from the second direction of view. The two angles $\alpha$ and $\beta$ define one plane in three-dimensional space. That plane is tangential to the interface between the PTV and OAR.

The preferred embodiment of the invention will then generate a two-dimensional histogram of the number of voxels in w a function of $\alpha$ and $\beta$ giving a Radiation Oncologist complete information about the optimum plane that selected beam orientations should be parallel to in order to be able to separate the PTV from the OAR with high accuracy.

With radiation delivered from a gantry that can rotate a full circle about the isocenter (a three-dimensional rotation center usually placed at the centroid of the PTV) and a patient table that can rotate about that same isocenter in a semi-circle, beam orientations that will fulfill the requirements of being parallel to the optimum plane can be obtained as a continuum of gantry-table positions by a simple coordinate transformation. In the preferred embodiment, those gantry-table positions are presented to the Radiation Oncologist either as a numerical table, or graphically on a computer screen and he/she can select a number of non-conflicting angles for the therapy. Alternatively, they could be the input to other computer programs that further select beam orientation.

The preferred embodiment recognizes that the interface between the PTV and OAR may not be characterized well by a single optimum plane. In that case, the two-dimensional histogram of number of voxels in w a function of $\alpha$ and $\beta$ will be more complex than showing only a single peak. The judgment of the Radiation Oncologist will then be necessary in order to select more than one pair of [$\alpha$,$\beta$] values and their corresponding optimum planes.

An alternative method and apparatus for selecting optimum beam orientations is a computer running a program that finds the overlap between an adjacent PTV and OAR by using techniques other than Gaussian Invariants, like extending the PTV and OAR in three-dimensions by a certain number of voxels, or by other measures of proximity.

Yet another alternative method and apparatus for selecting optimum beam orientations is a computer running a program that determines the tangent vectors in the interface between the PTV and the OAR by techniques other than Gaussian Invariants, like a search of directions of PTV and/or OAR voxels over a neighborhood.

Yet another alternative method and apparatus for selecting optimum beam orientations is a computer running a program that communicates the preferred plane angles by methods other than a two-dimensional histogram of number of voxels as a function of angles $\alpha$ and $\beta$, like by audio or other visual representations.

A primary object of the present invention is to assist in the selection of optimum angles or optimum arcs in radiation therapy planning, specifically in clinical cases in which one or more OARs are adjacent to the PTV.

Another object of the invention is to analyze the interface between a PTV and an adjacent OAR in such a way that a plane or group of planes can be mathematically defined that separate the two regions.

Another object of the invention is to determine a set or sets of gantry-table angles such that beams with the corresponding orientations are parallel to the optimum plane or planes, effectively allowing the full irradiation of the PTV with minimum damage to the OAR.

An advantage of this invention is that its goal is limited to a set of operations that will be useful in defining optimum beam orientations for radiation treatment that a computer can carry out fast and effectively in a clinically useful time.

Another advantage of the invention is that the nature of the calculations to be carried out and of the interactive displays to be generated is such that they can be easily incorporated in commercial software treatment plans.

Yet another advantage of the invention is that its use does not rely on complex mathematical operations that exclude the judgment of the Radiation Oncologist and, in fact, it relies on that judgment to make a final selection of beam angles or arcs, guided by computer graphics that are usually already incorporated into available commercial radiation treatment planning software packages.

Yet another alternative advantage of the invention is that the resulting optimal plane or planes can form a subset of all possible delivery orientations from a source that can travel over the surface of a sphere and that smaller subset can be used as input to an automatic beam selection algorithm, if desirable.

Other objects, advantages and novel features will be set forth in part in the following portions of the specification, wherein the detailed description is for the purpose of fully disclosing the preferred embodiment of the invention, without placing limitations thereon.

BRIEF DESCRIPTION OF THE DRAWINGS

The accompanying drawings, which are incorporated into and form part of the specification, illustrate the preferred embodiment of the invention and, together with the description and one example, serve to explain the principles of the invention. The drawings are only to illustrate the preferred embodiment of the invention and are not to be construed as limiting the invention.

FIG. 13 describes axial and saggital views of the phantom of FIG. 4 if it were rotated in the same way as the "fan" of FIG. 6b would have to be rotated to be identical to the "fan" of FIG. 6a.

DESCRIPTION OF THE PREFERRED EMBODIMENT

Figure 1:
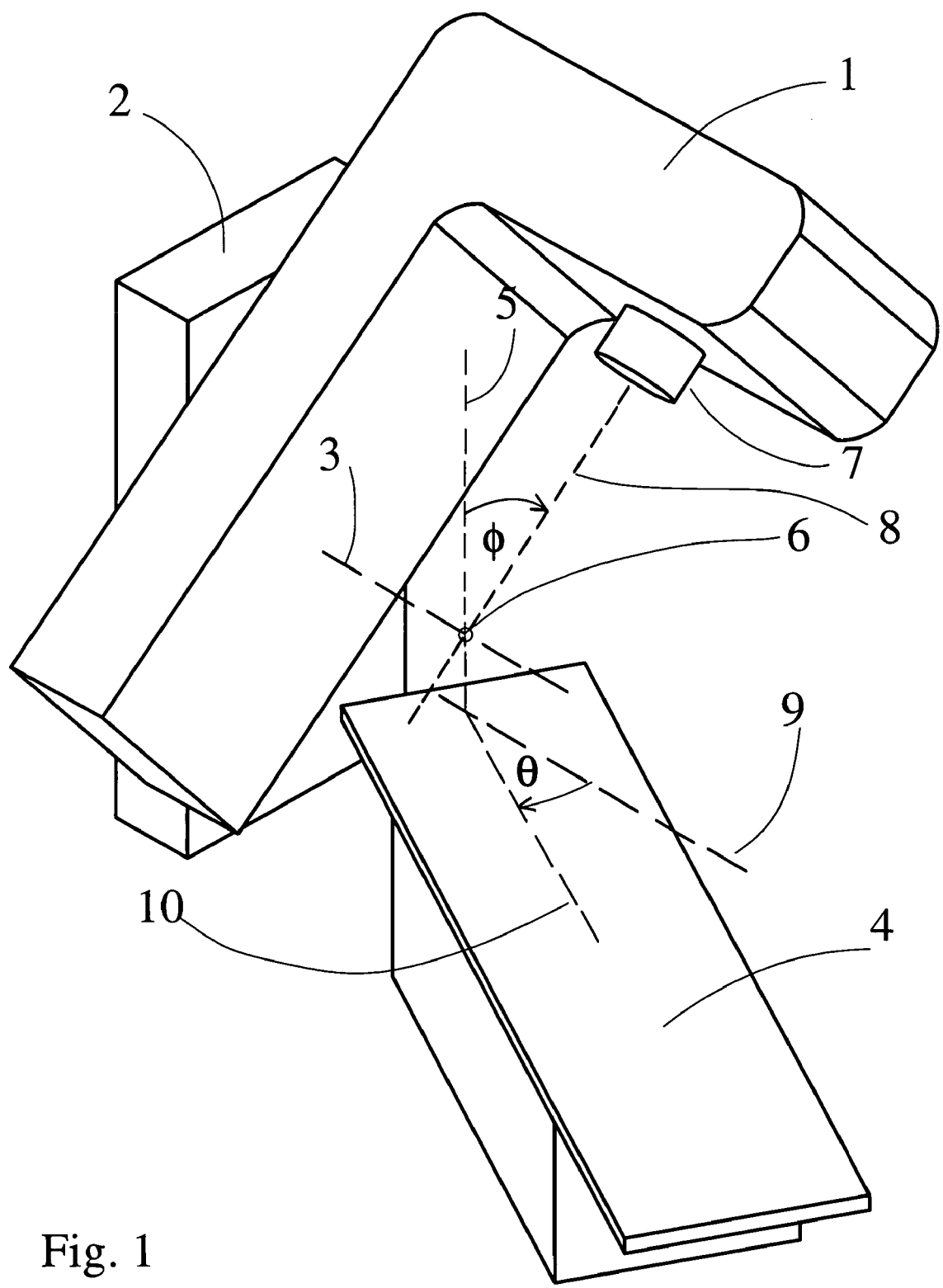
FIG. 1 is a perspective view of the environment in which the present invention can be used and defines the gantry and the table angles by which those elements can rotate.

Referring to FIG. 1, the environment of the present invention is shown as a schematic drawing of a radiation therapy room in which a gantry 1 is attached to a support 2 by an appropriate system of bearings. Support 2 is fixed to the therapy room floor while gantry 1 can rotate about a horizontal gantry rotation axis 3. A patient table 4 is mounted on the therapy room floor with an appropriate mechanism that allows it to rotate about a vertical table rotation axis 5. The intersection of the gantry rotation axis 3 and the table rotation axis 5 defines the room isocenter 6. A radiation source built into the gantry 1 emits controlled amounts of radiation from a collimator 7 with rays that are parallel to the source central axis 8. The source central axis 8 intersects both the gantry rotation axis 3 and the table rotation axis 5 at the isocenter 6. In modern radiation therapy, the collimator 7 can be a complex mechanism that not only delimits the radiation field to a set of desired contours, but can also change its apertures dynamically as needed by the chosen modality of radiation delivery. The angle between the table rotation axis 5 and the source central axis 8 is the gantry angle φ, positive as indicated by an arrow. The gantry can rotate with values of $-180°<\phi\leq180°$, except for possible collisions between the gantry and the table. The angle between a line 9 parallel to the gantry rotation axis 3 on the plane of table 4 and the central longitudinal line 10 of table 4 is the table angle θ, positive as indicated by an arrow. The table can rotate between $-90°\leq\theta\leq90°$, except for possible collisions. A patient is immobilized on the patient table 4 during therapy, placed in such a way that a specified point in the volume to be irradiated coincides with isocenter 6. That point can be the centroid of a tumor, for example.

Figure 2:
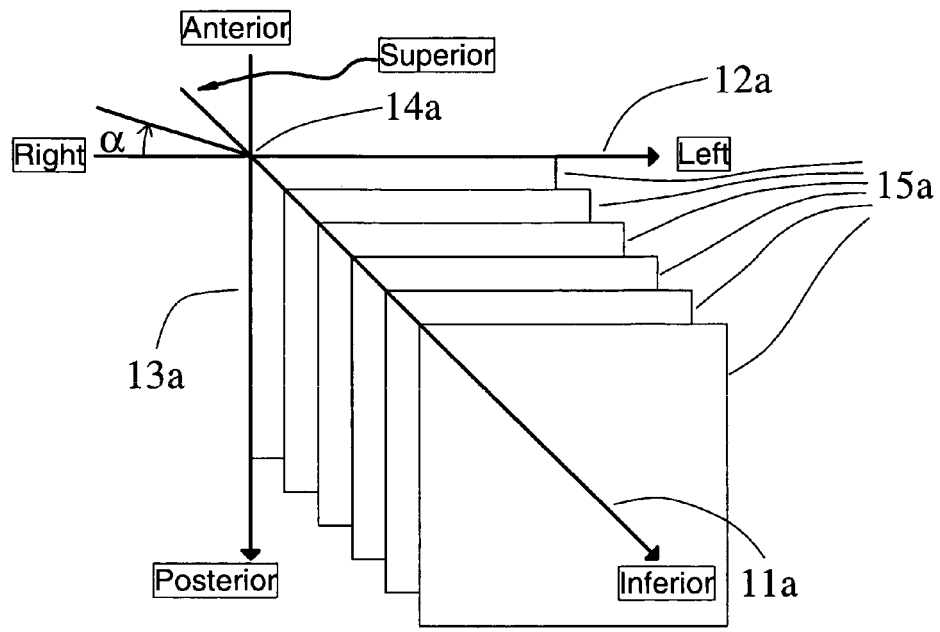
FIG. 2 is a description of the patient coordinate system leading to axial views of the relevant anatomy planes.

FIG. 2, is a view of a three-dimensional orthogonal coordinate system that is anchored to the patient table 4. The Superior-Inferior axis 11a is parallel to the central longitudinal line 10 of table 4. A patient would normally be placed on table 4 with the head towards the Superior direction and the feet towards the Inferior direction. The Right-Left axis 12a coincides then with the position of the patient's right and left arms and the Anterior-Posterior axis 13a corresponds to the front and back portions of the patient's anatomy. The point of intersection of the three axes 14a coincides with the isocenter 6 of the therapy room. The portion of the patient's anatomy that is relevant for radiation therapy is represented by a three-dimensional array of voxels formed by a number of sectioning planes 15a, each plane being a two-dimensional array of voxels. The view of each plane 15a seen by an observer is an axial view of the patient's anatomy. Only the Posterior-Left quadrants of the planes 15a are shown. Angle α will be described in connection with FIG. 4.

Figure 3:
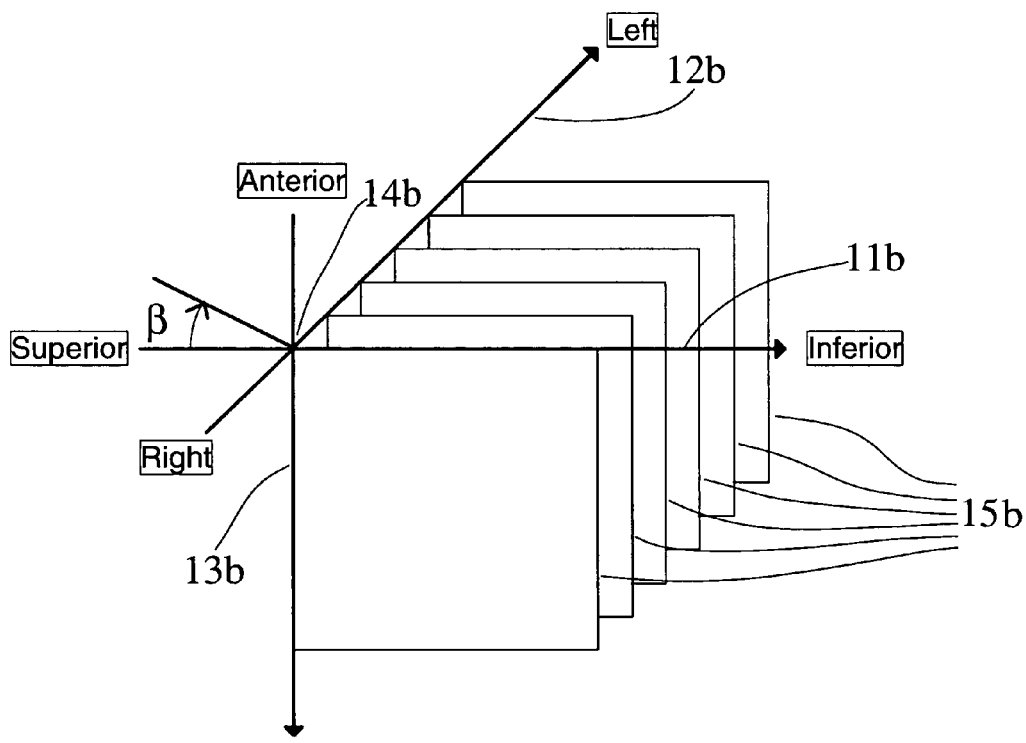
FIG. 3 is a description of the rotated patient coordinate system leading to saggital views of the relevant anatomy planes.

FIG. 3 is another view of the three-dimensional orthogonal coordinate system anchored to the patient table 4. The Superior-Inferior axis 11b, the Right-Left axis 12b and the Anterior-Posterior axis 13b are anchored to the patient table 4 in the same way as in FIG. 2. The point of intersection of the three axes 14b coincides with the isocenter 6 of the therapy room. The three-dimensional array of voxels relevant for radiation therapy has been sectioned by a different set of planes 15b. The view of each plane 15b is a saggital view of the patient's anatomy. Only the Posterior-Inferior quadrants of the planes 15b are shown. Angle β will be described in connection with FIG. 4.

Figure 4:
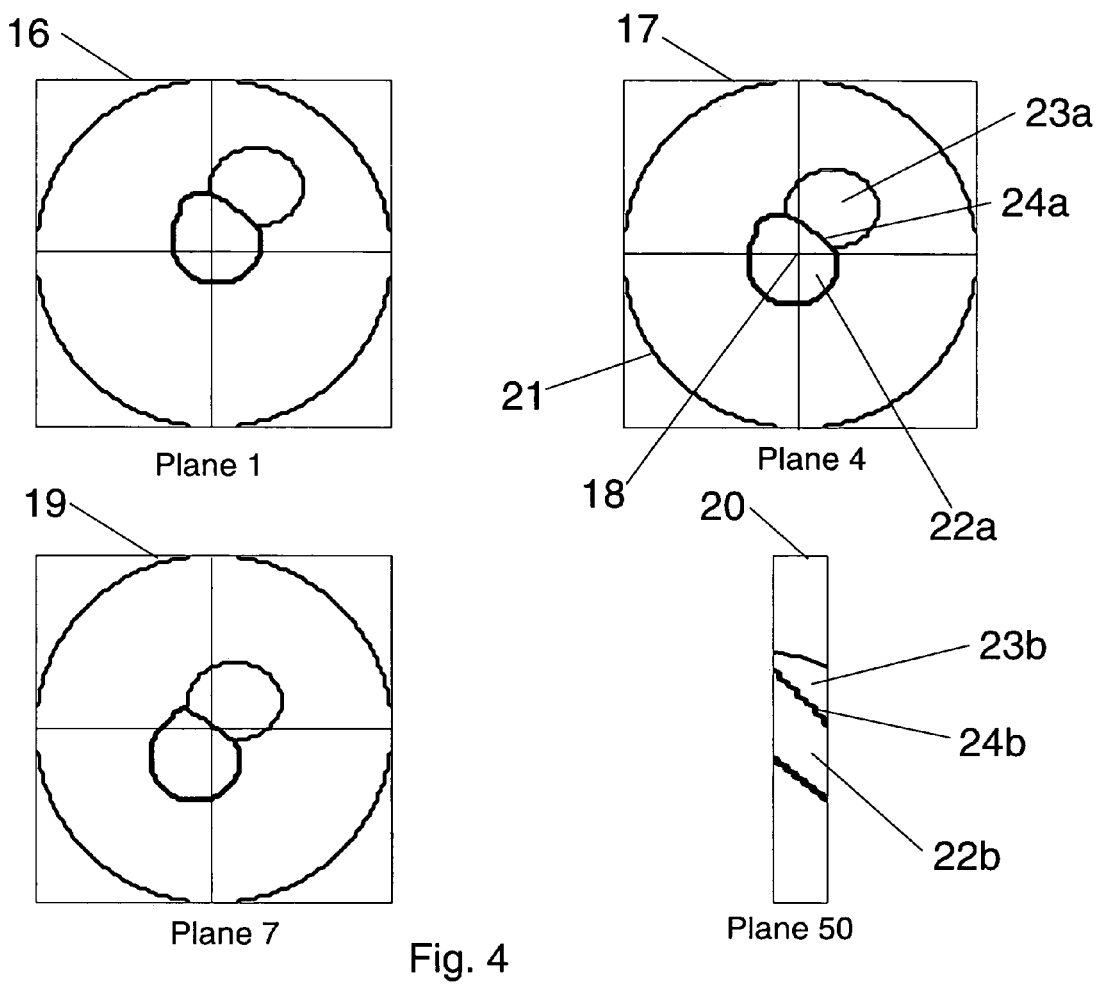
FIG. 4 is a graphical description of a three-dimensional phantom used to illustrate the function of the present invention.

FIG. 4 shows computer generated axial and saggital views of a three-dimensional mathematical phantom that will be used to illustrate the function of the present invention. The phantom consists of 7 axial planes of dimensions 200×200 mm with a thickness of 5 mm each. Each axial plane is divided into voxels of dimension 2×2×5 mm and is represented mathematically by a two-dimensional matrix of 100× 100 numbers. The Superior plane 16 is labeled Plane 1, the central plane 17 that contains the centroid 18 of the phantom is labeled Plane 4 and the Inferior plane 19 is labeled Plane 7. A near central plane 20 of the phantom in saggital view is labeled Plane 50. The description of the phantom will be made with reference to the central axial plane 17 and the saggital plane 20, as the interpretation of the other two views becomes obvious. The phantom consists of a cylinder of water 21 of 200 mm diameter. A Planning Target Volume (PTV) 22a and an adjacent Organ-at-Risk (OAR) 23a of water equivalent density have been defined near the center of the water cylinder 21. The objective of the radiation treatment is to deliver as close to 100% of the desired radiation dose to the PTV 22a while sparing the OAR 23a to the maximum extent possible. The interface 24a between the PTV 22a and the OAR 23a exhibits a boundary angle with respect to the horizontal in each of the axial views 16, 17 and 19 and in those views not shown. It is the initial objective of the invention to obtain automatically the value of that angle which defines boundary angle α in FIG. 2. The saggital view 20 of the phantom also shows the PTV 22b, the OAR 23b and the interface 24b between the PTV 22b and the OAR 23b. Since the PTV 22a and the OAR 23a are not located identically in the different axial views but are displaced downward and to the left as the plane number increases, the interface 24b also exhibits a boundary angle with respect to the horizontal in the saggital view 20 and in those views not shown. It is another objective of the invention to obtain automatically the value of that boundary angle which defines angle β in FIG. 3.

Figure 5:
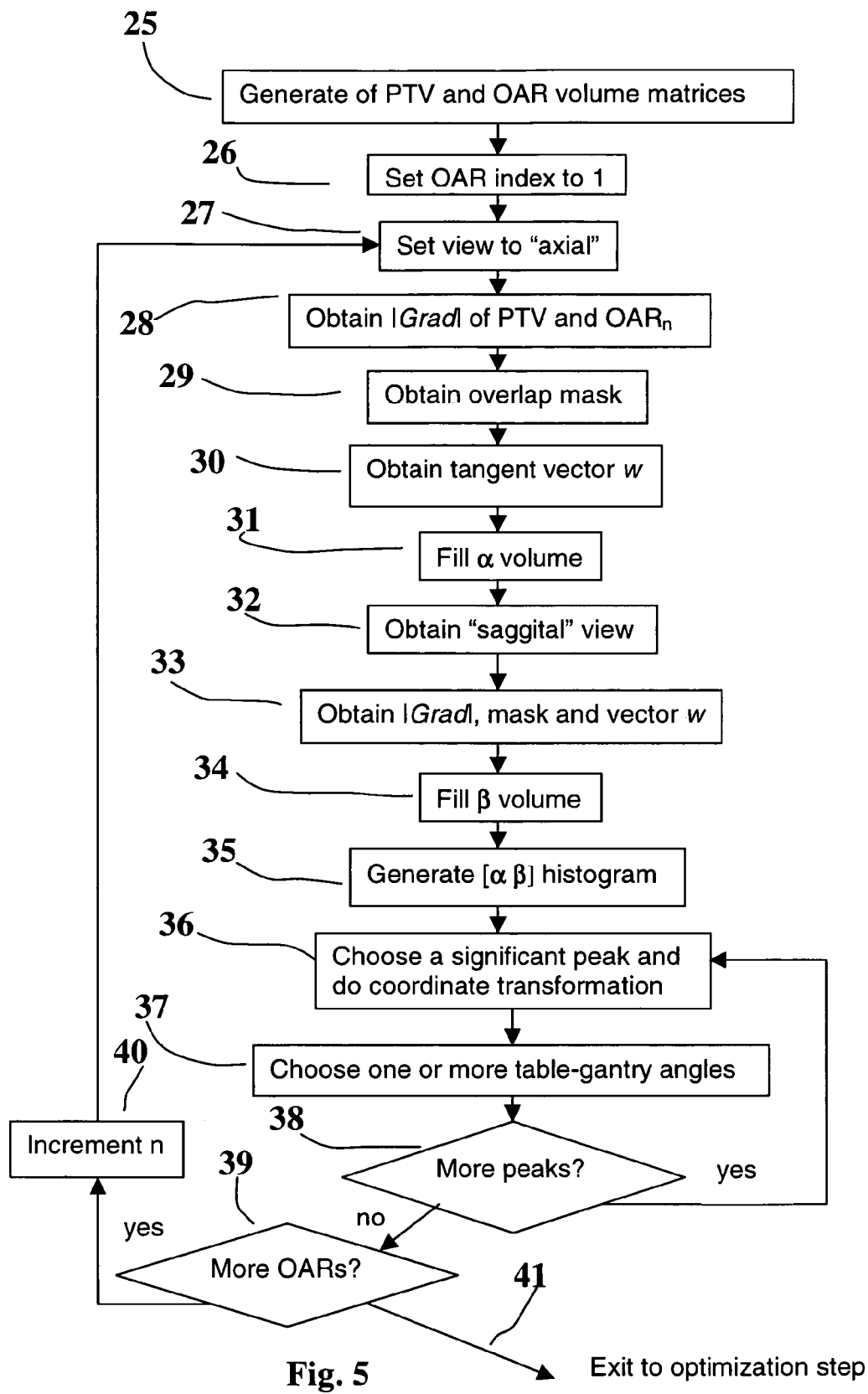
FIG. 5 is a flow diagram of the preferred process of assisted beam orientation selection in radiation therapy planning.

FIG. 5 is a flow diagram of the preferred process of assisted beam orientation selection in radiation therapy planning. In 25 three-dimensional matrices are formed to represent numerically the PTV and any number of OARs that are adjacent to the PTV in a particular patient anatomy. The number of adjacent OARs is expected to be relatively small, usually 1 and more rarely 2 or 3. Each adjacent OAR is numbered with a sequential index.

The three-dimensional matrix for the PTV is formed by initially setting all its values to zero and then setting those matrix elements that correspond geometrically to the PTV voxels equal to a constant density. The matrix for the PTV will be indicated by the density distribution $L^{PTV}$. Three-dimensional matrices for the OARs are formed in the same manner, using the same constant density as in the case of the PTV. The matrices for the density distributions of the OARs will be indicated by $L^{OARn}$ with n being the index of the corresponding OAR.

In 26, the OAR index is set to n=1 and in 27 $L^{PTV}$ and $L^{OARn}$ are rotated, if necessary, so that an axial view of the matrix is presented in each plane, as in FIG. 2 and in 17.

In 28, the first step to describe mathematically the interface between the PTV and OARn is carried out by obtaining a blurred version of their perimeters. The preferred method for that purpose is by calculating new |Grad| matrices of the density distributions $L^{PTV}$ and $L^{OARn}$ in three-dimensions by using the Laplacian operator of Gaussian Invariant theory $$|Grad|=\sqrt{L_x^2+L_y^2+L_z^2}$$

in which $L_x$ stands for the result of convolving a general density matrix L with the partial derivative with respect to x of a three-dimensional Gaussian with standard deviation δ, and similarly for the coordinates y and z. The axial views of the planes of the |Grad| matrices show blurred forms of the axial perimeters of the PTV and of OARn. The amount of blurring is controlled by the standard deviation δ of the Gaussian.

In 29, the overlap between the |Grad| for the PTV and that of OARn is calculated, resulting in a three-dimensional overlap matrix. A voxel in the overlap matrix is set to a logical 1 (TRUE) if the corresponding voxels in the two |Grad| matrices have a value above a certain threshold. Otherwise, the voxel is set to logical 0 (FALSE). The number of TRUE voxels in the overlap matrix is then reduced by requiring that a voxel remains TRUE only if was originally non-zero in the $L^{OARn}$ matrix. The result is a three-dimensional overlap mask of the voxels in OARn that are adjacent to the PTV.

In 30, a two-dimensional vector corresponding to the direction of the tangent to the interface 24a between the PTV and OARn is calculated at the position of each of the TRUE mask voxels. The preferred method for obtaining the tangent vectors is by use of the gauge coordinate w of Gaussian Invariant theory. The two-component tangent vector is given by $$w = \begin{bmatrix} L_y \\ -L_x \end{bmatrix}$$

in which L is now the masked |Grad| of the PTV. The $L_y$ component of each vector w corresponds to the x-coordinate of the tangent vector to the PTV in each particular voxel of the mask, while the $-L_x$ component corresponds to the y-coordinate.

In 31, a matrix is filled with the angles α at each of the TRUE voxels in the mask. Each angle α is calculated from the relationship $$\alpha = \tan^{-1}\left(\frac{y\text{-coordinate of } w}{x\text{-coordinate of } w}\right)$$

with appropriate corrections for the cases in which the denominator is zero. The resulting calculated values of the angle α are estimates of the angle α in FIG. 2.

In 32, the matrices $L^{PTV}$ and $L^{OARn}$ are rotated 90° about the Anterior-Posterior axis 13*a* in order to obtain two-dimensional planes with a saggital view of the patient's anatomy, as in FIGS. 3 and 20. In 33 the |Grad| matrices for the newly rotated PTV and OARn are obtained by the same method as in 28. The steps of 29 and 30 are then repeated with the rotated |Grad| matrices, except that the results of the $\tan^{-1}$ operation of 31 correspond now to estimates of the angle β in FIG. 3 at each of the voxels in the mask. In 34, a matrix is filled with the angles β at each of the TRUE voxels in the mask.

In 35, a two-dimensional histogram of the number of voxels that have all possible pairs of values α and β is generated. The two-dimensional bin size for the histogram is adjusted so that the results can be presented conveniently to a user, or interfaced to a radiation treatment planning program in a suitable manner.

In 36, a significant peak in the [α β] histogram is selected as indicative of a region in the interface 24*a* between the PTV 22*a* and an OAR 23*a* with a predominant pair of values for α and β. The selection can be done interactively from a graphic display or automatically by a suitable computer program. The selected [α β] pair leads to a continuum of pairs of gantry angles φ and table angles θ that can deliver radiation beams to the PTV with source central axes 8 that are parallel to the interface 24*a* between the PTV 22*a* and an OAR 23*a*. An appropriate beam shaping collimator 7 can then separate the PTV 22*a* from the OAR 23*a* at all points along the path of the radiation source rays.

The relationship between the selected values of [α β] and the [φ θ] angles is given by the coordinate frame transformation $$\phi = \tan^{-1}\frac{\cos\alpha\cos\beta}{\cos\beta\sin\alpha\cos\theta + \cos\alpha\sin\beta\sin\theta}$$

valid for the range −90°≦θ≦90° with appropriate simplifications when the denominator is zero. A choice is then made in 37 of one or more pairs of gantry angles φ and table angles θ and they are examined for conflicts with other therapy requirements in conjunction with a graphical representation of the PTV, OARs and other intervening organs or by other automatic or semi-automatic methods. The pairs of angles [φ θ] that are found most favorable for the needed therapy are saved in a list.

In 38, the question is asked whether the significant peak in the [α β] histogram selected in 36 is the only significant one or there are more. If there are more peaks to be considered, the process goes back to 36 and a new peak is selected. If there are no more significant peaks, a second question is asked in 39 on whether there are more adjacent OARs that have to be considered. If the answer is affirmative, the OAR index n is incremented by one and the process continues in 27. If there are no more OARs to consider, the assisted beam selection process exits to the optimization step in 41 with a list of gantry angles φ and corresponding table angles θ that can result in highly uniform dose distributions in the PTV and a minimum of dose being delivered to the OARs.

EXAMPLE

In order to illustrate and clarify the preferred embodiment of the invention, the optimization of an IMRT radiation treatment plan for the mathematical phantom of FIG. 4 will be described in detail. Initially, a standard optimization will be described, followed by a second optimization using the assisted beam orientation selection method of the present invention.

Figure 6A:
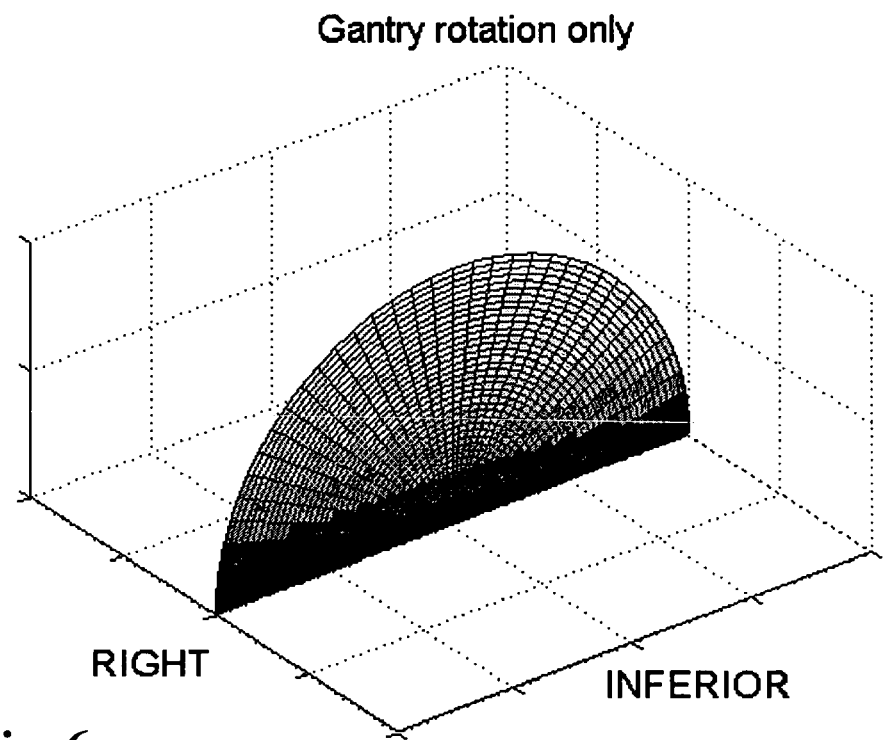
FIG. 6a shows a "fan" of center lines of beam orientations that can be achieved by rotation of the gantry only, leaving the table fixed.

From the work of T. Bortfeld and W. Schlegel in "*Optimization of beam orientations in radiation therapy: some theoretical considerations*", Physics in Medicine and Biology, Vol. 38, (1993), pp. 291–304 and that of S. Webb in "*Optimizing the planning of intensity-modulated radiotherapy*", Physics in Medicine and Biology, Vol. 39, (1994), pp. 2229–2246, which has been followed well by the Radiation Oncology profession in all the intervening years, a nine-beam co-planar treatment plan with equal angular spacing will be devised for the phantom of FIG. 4 placed on the patient table 4 with the phantom centroid 18 placed at the isocenter 6. The position of the phantom is such that Plane 1, 16, is towards the Superior direction of 11*a* and, correspondingly, Plane 7, 19, is towards the Inferior direction of 11*a*. The patient table 4 is assumed to be fixed at a table angle θ=0, FIG. 1, so that rotation of the gantry 1 describes a circle around the isocenter whose surface is parallel to the axial views 15*a*. FIG. 6*a* shows the upper half of a "fan" that describes the possible positions of the gantry 1 as it rotates around the isocenter, seen from the patient set of coordinates of FIG. 2, anchored to the patient table 4. Each radial direction shown corresponds to one of the gantry angles φ, which, for the purpose of presentation, have been spaced by 5°.

The selected beam angles φ have been 0, 40, 80, 120, 160, 200, 240, 280 and 320°. The Dynamically Penalized Likelihood (DPL) method described in J. Llacer, et al, "*Comparative Behaviour of the Dynamically Penalized Likelihood algorithm in inverse radiation therapy planning*", Physics in Medicine and Biology, Vol. 46, (2001), pp. 2637–2663 has been used for the optimization of the 769 beamlets into which the 9 beams have been divided. Each beamlet had a nominal cross section of 4×4 mm and the simulated therapy was done with X-rays from a linear accelerator with 6 Mv energy. The dose distributions that were required of the DPL algorithm were that the PTV should receive as close to 100% dose throughout and the OAR should not receive more than 60% dose at any point and that 40% dose should not be received by more than 15% of its volume.

Figure 7:
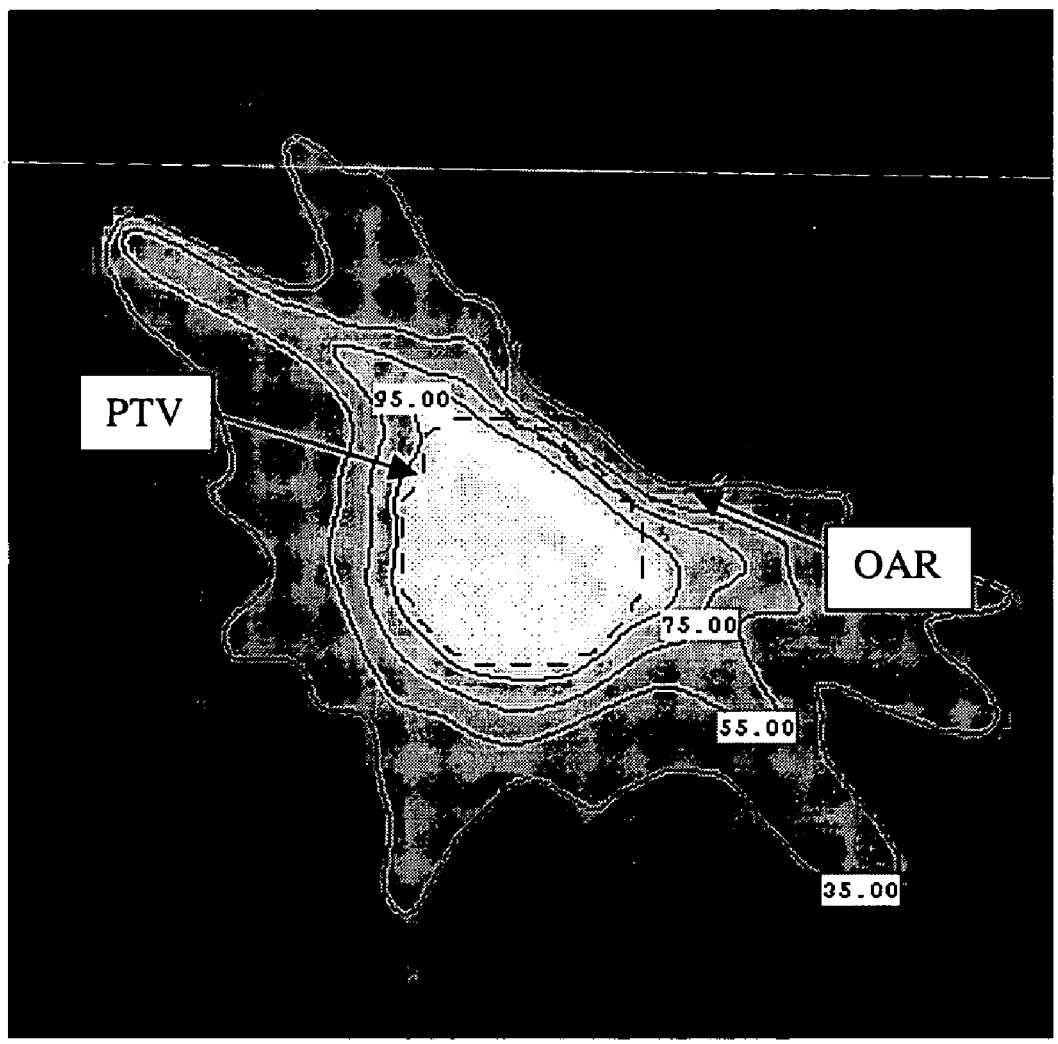
FIG. 7 is a raster image of the dose distribution delivered to the central axial plane of the example of FIG. 4 for a treatment plan optimized according to a standard beam selection. Isodose lines for 95%, 75%, 55% and 35% are shown.

FIG. 7 shows the radiation dose that would be delivered to the phantom at the central Plane 4, 17, if the DPL therapy plan were actually carried out. The PTV and OAR outlines are shown in broken black lines. The solid lines correspond to isodose lines, lines of equal dose, for 95%, 75%, 55% and 35% dose. The gray scale is such that 100% dose is white, 0% dose is black. It should be noticed that the PTV only receives between 75% and 95% dose in a substantial region near the interface with the OAR instead of the desired 100% throughout.

Figure 8:
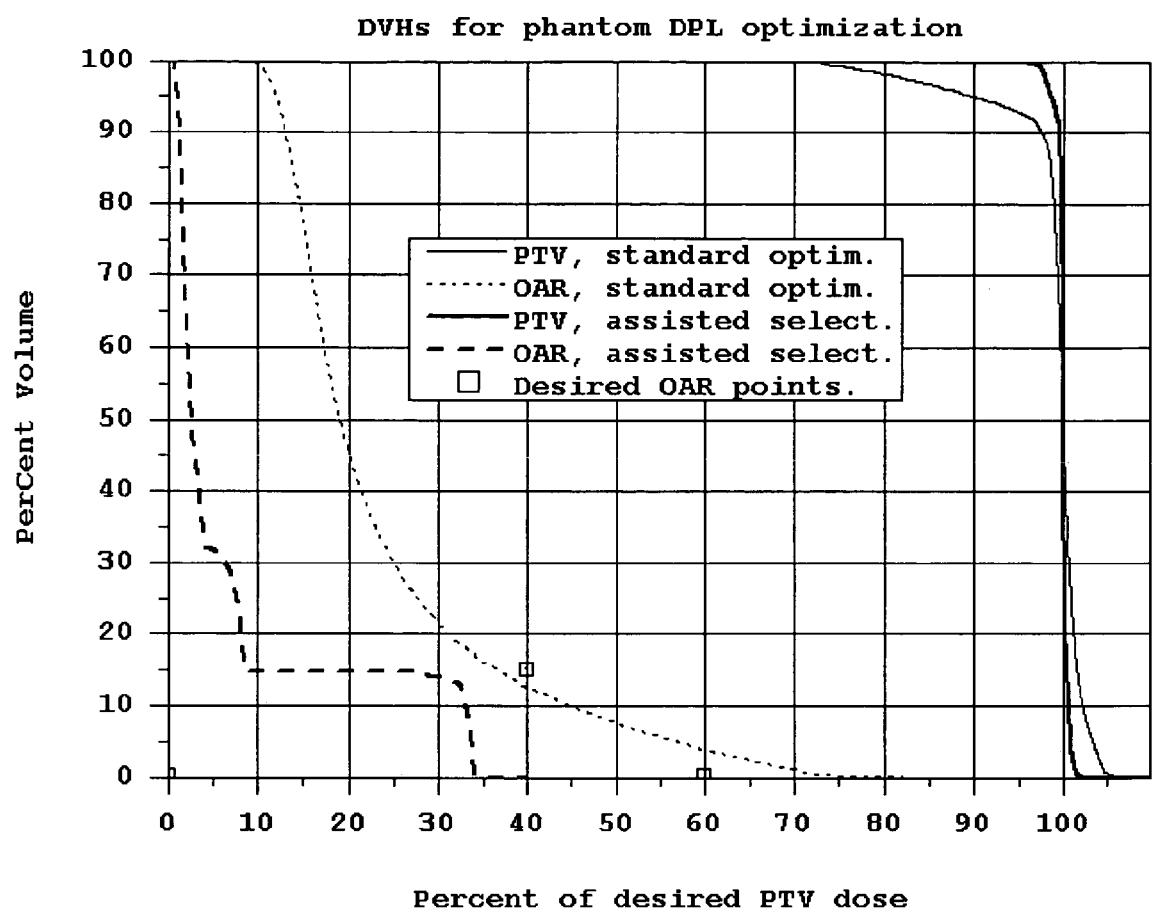
FIG. 8 is a graph of Dose-Volume Histograms (DVHs) resulting from a treatment plan optimized according to a standard beam selection and from an assisted beam orientation selection according to the method of the current invention.

One of the most useful tools for assessing the quality of a radiation distribution is the Dose-Volume Histogram (DVH), which shows what fraction of a particular region's volume receives more than a particular dose. FIG. 8 shows the DVHs for the PTV and OAR of the phantom with the results of the standard optimization shown in thin solid or broken lines, respectively. As an example of its use, note that only 95% of the PTV volume receives more than 90% of the desired dose. The desired DVH dose points for the OAR are shown by two squares and it is clear that the desired maximum dose of 60% to the OAR is not satisfied, although the second requirement of no more than 15% of the OAR volume should receive more than 40% dose is being satisfied. The long tail on the upper left DVH for the PTV is representative of under-dosing of a tumor and is generally not acceptable because of danger of tumor recurrence in a real patient.

Figure 9A:
FIG. 9a is a raster image of the magnitude of the gradient of the center plane of the Planning Target Volume (PTV) of the phantom of FIG. 4, with blurring by a Gaussian Invariant operator.
Figure 9B:
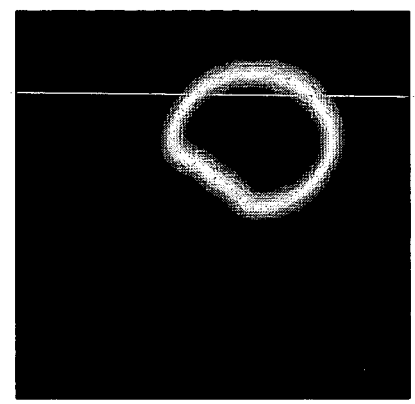
FIG. 9b is the corresponding image for the Organ-at-Risk (OAR) of the same phantom.
Figure 9C:
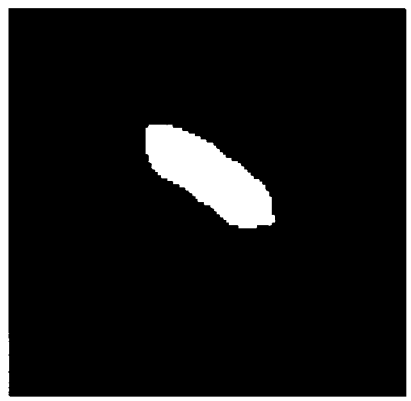
FIG. 9c is a Boolean image (ones and zeros) of the overlap between the FIGS. 9a and 9b.
Figure 9D:
FIG. 9d is a Boolean image of a "mask", the overlap of FIG. 9c that falls inside the OAR.
Figure 10A:
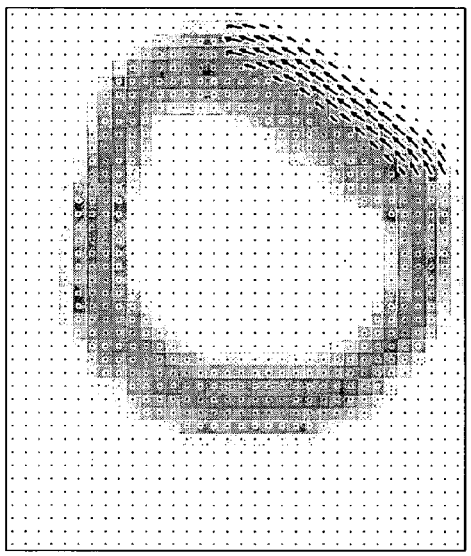
FIG. 10a is a composite of the axial raster image of FIG. 9a in a soft gray scale and a number of arrows (one per voxel) in the mask that graphically describe the boundary angles of the interface between the PTV and the OAR. Single dots correspond to single voxels outside the mask.
Figure 10B:
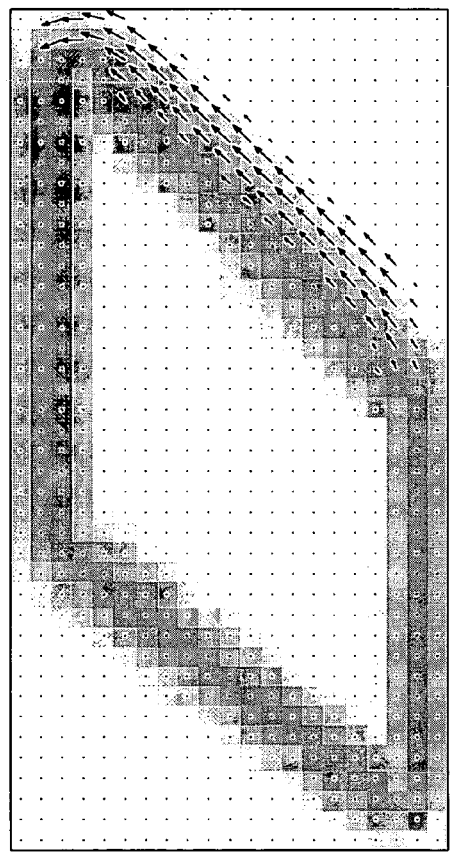
FIG. 10b is the corresponding raster image for the central saggital plane.

For the assisted selection of beam orientation angles of the present invention, with the phantom placed on the patient table as described above, the |Grad| matrices for the PTV and the single OAR are first obtained, 28. FIG. 9a shows an image of the central |Grad| plane for the PTV and FIG. 9b shows the corresponding result for the OAR. The overlap plane is shown in FIG. 9c. The overlap is considered TRUE if both the |Grad| for the PTV and OAR have a value above 1% of their respective maxima. The mask 29 is shown in FIG. 9d. FIG. 10a shows a medium gray image of the same central |Grad| plane for the PTV of FIG. 9a, together with a group of small arrows (one arrow per voxel) whose direction is the tangent vector w obtained at 30 for the interface between the PTV and the OAR in axial view. The angles determined by the arrows correspond to the angles $\alpha$ that are placed in a matrix in 31. After obtaining the saggital view of the phantom in 32, the |Grad| and tangent vector w are obtained again, leading to a new set of arrows shown in FIG. 10b that are stored in a matrix of $\beta$ values, 33 and 34.

Figure 11A:
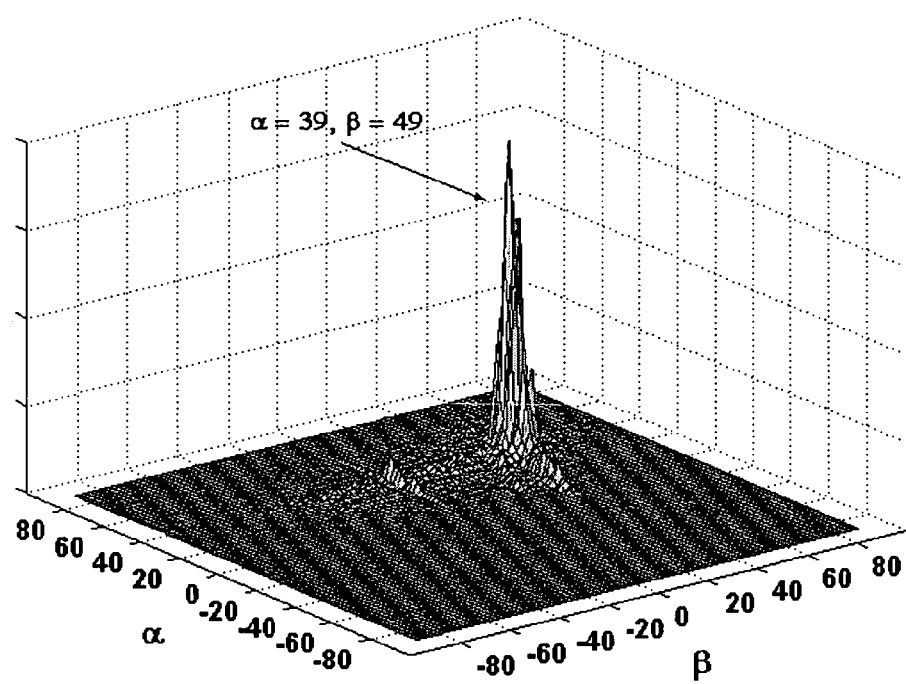
FIG. 11a is a two-dimensional histogram showing the number of voxels (vertical scale) that have tangent angles [α β] in [axial saggital] views between the PTV and the OAR of the phantom of FIG. 4.
Figure 11B:
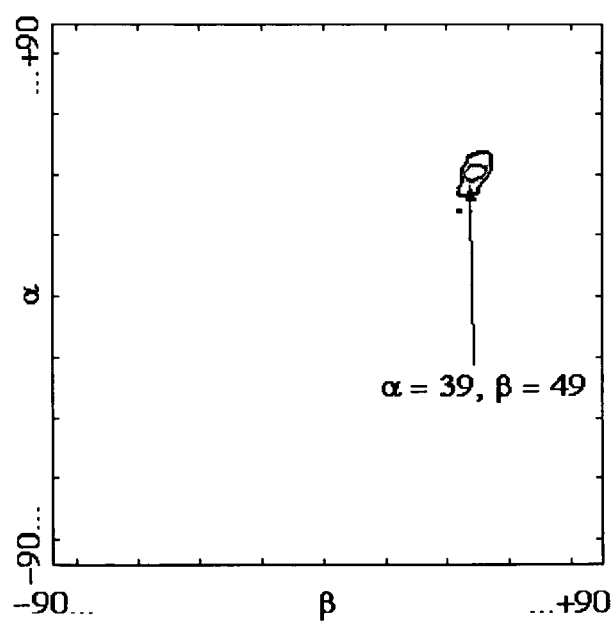
FIG. 11b shows an alternative presentation of the histogram as a topographical map with contours indicating the position of the peak.

FIG. 11 shows two different presentations of the [$\alpha$ $\beta$] histogram of 35. FIG. 11a shows a three-dimensional presentation of the number of voxels (vertical scale) that have a pair of values [$\alpha$ $\beta$] in the matrices of $\alpha$, 31, and $\beta$, 34. FIG. 11b shows a "topographic" view of the same histogram that may make the position of the peak easier to measure. The resulting pair of angles [$\alpha$ $\beta$] for the principal peak of the histogram is, approximately, [39° 49°], which will be used as the position of the significant peak of 36.

Figure 6B:
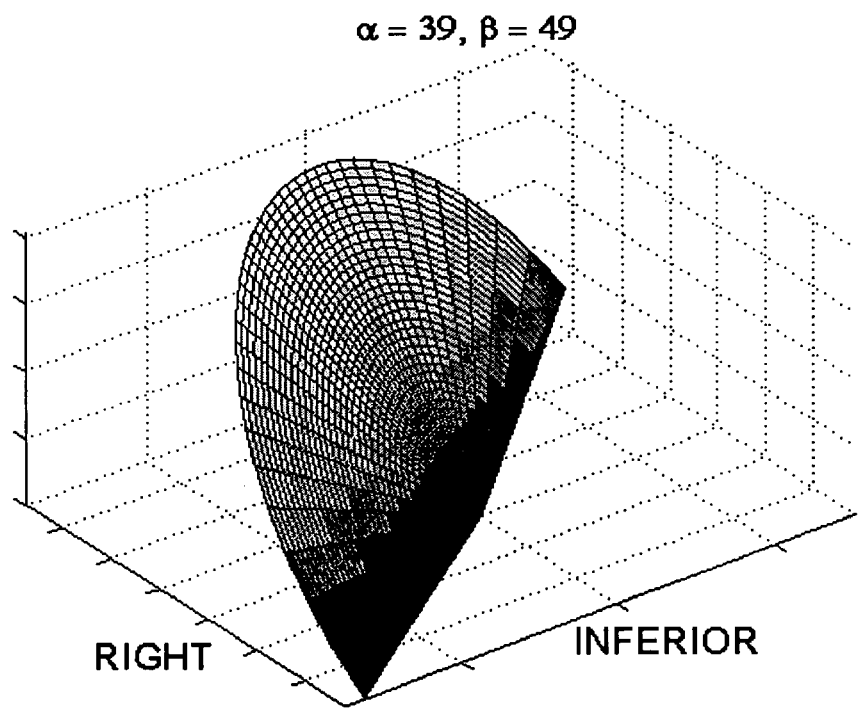
FIG. 6b shows the corresponding fan that results in optimum beam orientation selection for the example of FIG. 4.
Figure 12:
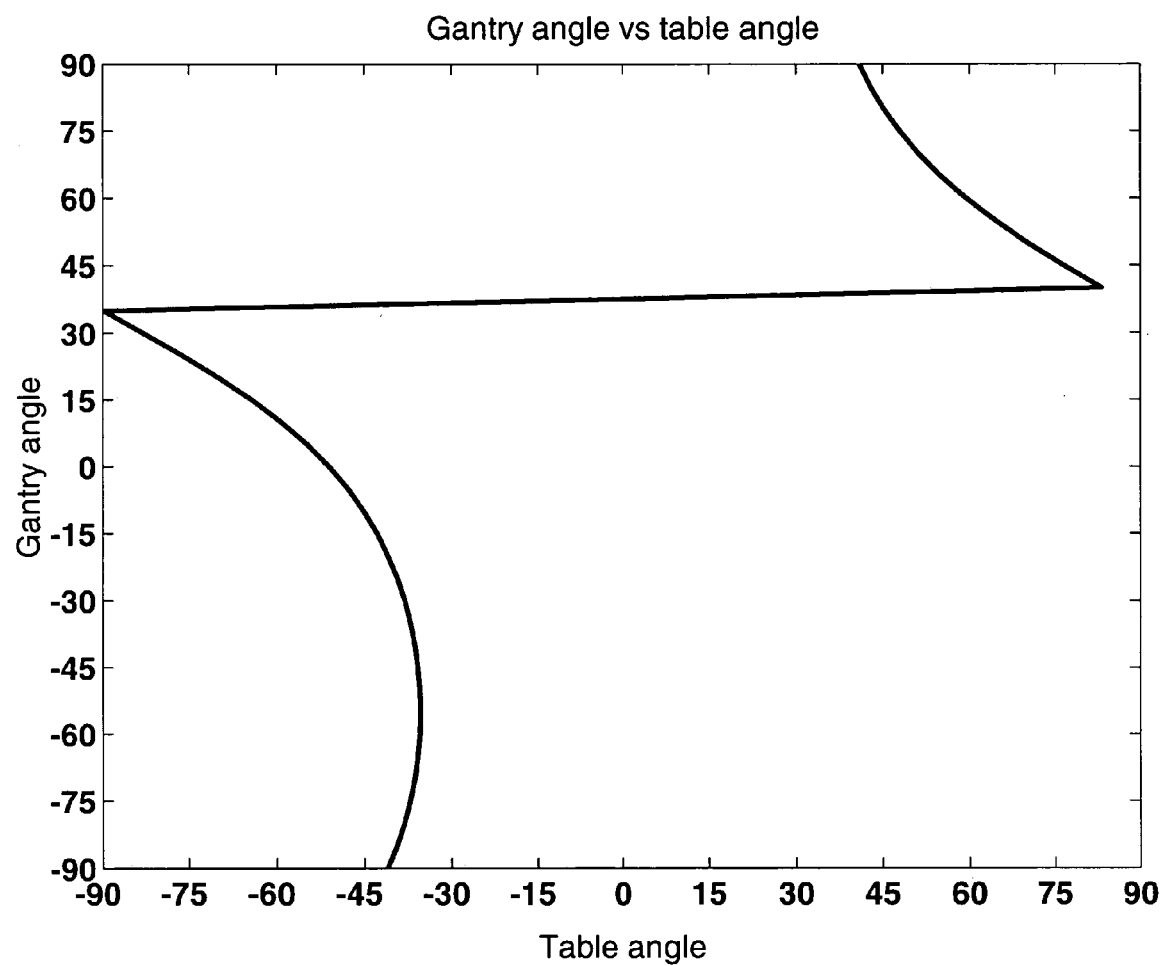
FIG. 12 is a graph of the pairs of [gantry table] angles that will allow the delivery of radiation with beam orientations whose center line is in the "fan" shown in FIG. 6b.

FIG. 12 shows a graph of the gantry angles $\phi$ as a function of table angle $\theta$ that are obtained at 36 by the [$\alpha$ $\beta$] to [$\phi$ $\theta$] coordinate transformation. FIG. 6b shows the upper half of the "fan" of beam directions that would now be seen from the fixed set of coordinates anchored to the patient table 4. Nine equally spaced angles have been chosen at 37 from the complete circular fan for the assisted beam orientation selection therapy plan.

Figure 13:
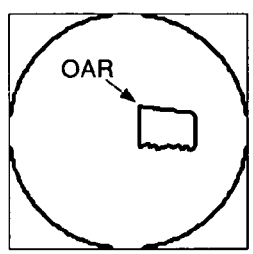
Figure 13:
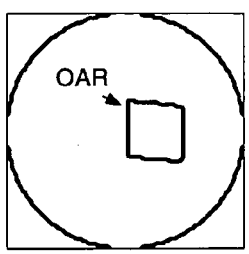
Figure 13:
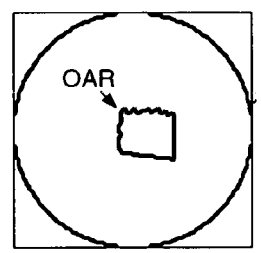
Figure 13:
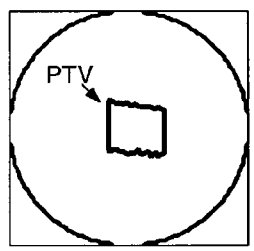
Figure 13:
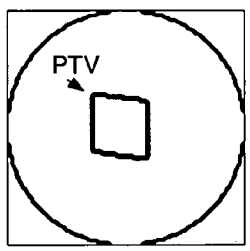
Figure 13:
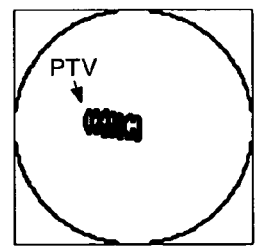
Figure 13:
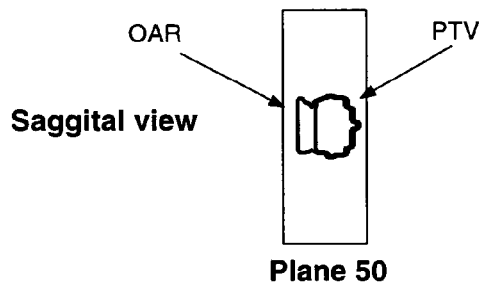

FIG. 13 clarifies why therapy beams selected from the fan of FIG. 6b are superior to those selected from the fan of FIG. 6a. If one were to rotate the phantom on the patient table in three-dimensions in the same way that the fan of FIG. 6b would have to be rotated to appear like that of FIG. 6a, optimum therapy could be achieved with rotation of the gantry alone. It is possible to rotate a mathematical phantom in three dimensions, but not a patient in a treatment room, in general. The axial view of the rotated phantom now has the OAR exclusively between Planes 1 and 6 and the OAR in Planes 7 to 13. In the saggital view of Plane 50, the OAR is totally separated from the PTV and this separation holds in all planes. For any radiation field whose center line 8 is parallel to the new axial planes, a multi-leaf collimator like the one discussed in FIG. 1a of U.S. Pat. No. 5,818,902 of Cedric X. Yu, for example, allows a radiation field to be shaped as the perimeter of a PTV and can, therefore, fully separate the PTV from the OAR.

Figure 14:
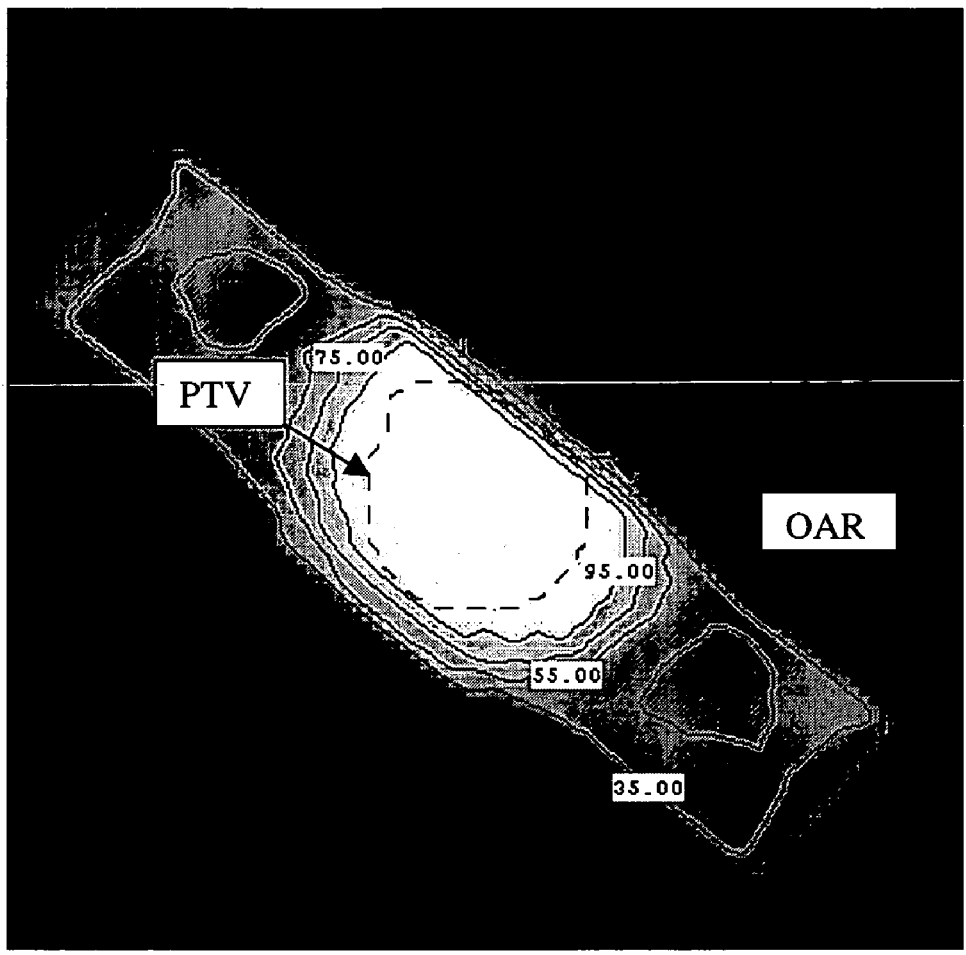
FIG. 14 is a raster image of the dose distribution delivered to the central axial plane of the example of FIG. 4 for a treatment plan optimized according to the assisted beam orientation selection of the present invention. Isodose lines for 95%, 75%, 55% and 35% are shown.

FIG. 14 shows the dose distribution achieved with the assisted beam orientation selection of the present invention using the DPL algorithm and the same dose requirements for the PTV and OAR. It must be noted that the boundary region between the PTV and OAR shows a rapid drop in dose near the edge between 95% and 55%. The dose to the OAR voxels is well below 55% throughout. The DVH for the improved optimization is shown in FIG. 8 with thick solid and broken lines and it clearly shows that the PTV suffers only a very small under-dosing tail (upper left of the curve for the PTV) and that the requirements for the OAR have been amply met.

Although the advantages of the invention have been demonstrated in detail, a number of changes, substitutions and alterations can be made without departing from the principle and scope of the invention.

I claim:

1. A method for selecting beam orientations in radiation therapy enabling the delivery of improved dose distributions to a planning target volume, while delivering a minimum dose to adjacent organs at risk, said method comprising the steps of:
    a) calculating the boundary angles that the interfaces between said planning target volume and said adjacent organs at risk subtend with respect to different axes of the coordinate system used for describing the patient's anatomy,
    b) transforming said boundary angles to a plurality of gantry and table angles, and
    c) selecting one or more pairs of said gantry and table angles from said plurality of gantry and table angles.

2. The method of claim 1, wherein said step of calculating boundary angles includes finding a mathematical description of said interfaces and determining the tangent angles of lines parallel to said interfaces.

3. The method of claim 2, wherein the mathematical description of said interfaces includes finding the proximity regions in three-dimensional space in which said planning target volume is closest to said adjacent organs at risk.

4. The method of claim 3, wherein said proximity regions are found by obtaining the overlap between blurred versions of the perimeters of said planning target volume and said adjacent organs at risk.

5. The method of claim 2, wherein determining said tangent angles includes a mathematical analysis of the neighborhood of voxels of said interfaces.

6. The method of claim 5, wherein said mathematical analysis includes the calculation of gauge coordinates in gaussian invariant theory.

7. The method of claim 1, wherein said plurality of pairs of gantry and table angles is obtained from said boundary angles by a coordinate transformation between said boundary angles that are measured in a coordinate system anchored to the patient anatomy and said gantry and table angles that are measured in a coordinate system anchored to the therapy room.

8. An apparatus for the assisted selection of beam orientations in radiation therapy enabling the delivery of improved dose distributions to a planning target volume, while delivering a minimum dose to adjacent organs at risk, said apparatus comprising:
    a) means for calculating the boundary angles that the interfaces between said planning target volume and said adjacent organs at risk subtend with respect to different axes of the coordinate system used for describing the patient's anatomy, b) means for transforming said boundary angles to a plurality of gantry and table angles.

c) means for selecting one or more pairs of said gantry and table angles from said plurality of gantry and table angles.

9. The apparatus of claim 8, wherein said means for calculating boundary angles includes means for finding a mathematical description of said interfaces and for determining the tangent angles of lines parallel to said interfaces.

10. The apparatus of claim 9, wherein the means for finding a mathematical description of said interfaces includes a mathematical procedure for finding the proximity regions in three-dimensional space in which said planning target volume is closest to said adjacent organs at risk.

11. The apparatus of claim 10, wherein said procedure for finding said proximity regions includes obtaining the overlap between blurred versions of the perimeters of said planning target volume and said adjacent organs at risk.

12. The apparatus of claim 9, wherein said means for calculating said tangent angles includes a mathematical analysis of the neighborhood of voxels of said interfaces.

13. The apparatus of claim 12, wherein said mathematical analysis includes the calculation of gauge coordinates in gaussian invariant theory.

14. The apparatus of claim 8, wherein said means for transforming said boundary angles to gantry and table angles includes a coordinate transformation between said interface angles that are measured in a coordinate system anchored to the patient anatomy and said gantry and table angles that are measured in a coordinate system anchored to the therapy room.

* * * * *